(12) United States Patent
Hara et al.

(10) Patent No.: US 7,084,182 B2
(45) Date of Patent: Aug. 1, 2006

(54) PHOTOPOLYMERIZATION INITIATOR

(75) Inventors: Tadashi Hara, Tokyo (JP); Takeshi Suzuki, Ibaragi-ken (JP); Rumiko Shimada, Ibaragi-ken (JP); Hideki Kazama, Tokyo (JP); Hironobu Akizumi, Tokyo (JP); Mutsumi Kashimura, Tokyo (JP)

(73) Assignees: Tokuyama Corporation, Yamaguchi (JP); Tokuyama Dental Corporation, Tokyo (JP)

( * ) Notice: Subject to any disclaimer, the term of this patent is extended or adjusted under 35 U.S.C. 154(b) by 50 days.

(21) Appl. No.: 10/797,060

(22) Filed: Mar. 11, 2004

(65) Prior Publication Data

US 2004/0180983 A1   Sep. 16, 2004

(30) Foreign Application Priority Data

Mar. 13, 2003  (JP) .............................. 2003-068737
Jul. 3, 2003    (JP) .............................. 2003-191397
Aug. 8, 2003   (JP) .............................. 2003-206867

(51) Int. Cl.
*A61K 6/83*   (2006.01)
*C08F 2/50*   (2006.01)

(52) U.S. Cl. ............................ 522/14; 522/16; 522/26; 523/115; 523/116

(58) Field of Classification Search .................. 522/14, 522/16, 26; 523/115, 116
See application file for complete search history.

(56) References Cited

U.S. PATENT DOCUMENTS 5,545,676 A * 8/1996 Palazzotto et al. ............. 522/15
6,063,830 A   5/2000 Deguchi et al.
6,133,338 A * 10/2000 Kimura et al. ............... 523/116
6,387,981 B1 * 5/2002 Zhang et al. ................ 523/117
6,528,555 B1 * 3/2003 Nikutowski et al. ......... 523/116
6,759,449 B1 * 7/2004 Kimura et al. ............... 523/118
6,899,948 B1 * 5/2005 Zhang et al. ................ 428/331

FOREIGN PATENT DOCUMENTS

EP    0 896 043    10/2002
EP    1 249 221    10/2002

OTHER PUBLICATIONS

Wayne D. Cook: "Photopolymerization kinetics of dimethacrylates using the camphorquinone/amine initiator system", Polymer, vol. 33, No. 3, 1992 pp. 600-609.

* cited by examiner

*Primary Examiner*—Susan Berman
(74) *Attorney, Agent, or Firm*—Sherman & Associates

(57) ABSTRACT

A photopolymerization initiator comprising (A) an α-diketone compound such as camphorquinone, (B1) an aliphatic amine compound such as triethanolamine or N-methyldiethanolamine, (B2) an aromatic amine compound such as ethyl p-dimethylaminobenzoate or N,N-dimethyl p-toluidine, and (C) a triazine compound substituted with a trihalomethyl group, such as 2,4,6-tris(trichloromethyl)-s-triazine or 2-phenyl-4,6-bis(trichloromethyl)-s-triazine. The photopolymerization initiator remains stable against the environmental light such as the indoor illumination light from a fluorescent lamp or the dental light illuminating the interior of the oral cavity, is excellently handled, is quickly cured by the irradiation with an intense light emitted from a light irradiator for polymerization, provides a cured body having excellent properties, can be stably preserved even at high temperatures, and is very useful as a dental composite resin.

6 Claims, No Drawings

PHOTOPOLYMERIZATION INITIATOR

BACKGROUND OF THE INVENTION

1. Field of the Invention

The present invention relates to a novel phopolymerization initiator useful for dental materials, photoresist materials, printing plate materials and hologram materials and, particularly, for dental materials. More specifically, the invention relates to a photopolymerization initiator which remains stable against the environmental light (having weak intensity) as compared to the conventional photopolymerization initiators but which quickly completes the polymerization in a very short period of time upon the irradiation with the intense light from such an irradiator as a halogen lamp, a xenon lamp or a laser diode, making it possible to obtain highly cured bodies, and without decreasing activity even after preserved for extended periods of time.

2. Description of the Related Art

There have been proposed a variety of photopolymerization initiators that generate radicals or ionic species upon the irradiation with the light to polymerize the polymerizable unsaturated compounds and cyclic compounds. In general, study has been forwarded concerning the photo-decomposition compounds that decompose upon absorbing the light to form polymerization activating species and systems of the photo-decomposition compounds combined with suitable photo-sensitizing agents, and such compounds have really been used.

As the photo-decomposition compounds, there have been known an acylphosphine oxide compound and an α-diketone compound. In particular, the α-diketone compound initiates polymerizing in the wavelength region of visible light which little affects the human body (e.g., a camphorquinone which is a representative α-diketone is a yellow compound having a maximum absorption wavelength of 468 nm). Further, a well-known combination of the photo-decomposition compound and the photo-sensitizing agent is the one of the α-diketone compound and a tertiary amine-compound. The above combination is useful in the field of dental materials since the α-diketone compound initiates polymerizing in the wavelength region of visible light.

In the field of dental materials, the above photopolymerization initiator is added to a paste-like composition (usually called composite resin) comprising chiefly a (meth)acrylate monomer and an inorganic filler to impart photopolymerizing property to the composite resin. The composite resin in the state of a paste is molded into the shape of a tooth and is cured by being irradiated with the light from a special light irradiator. Hereinafter, the light irradiated for curing by polymerization is often called "active light". In general, the active light is emitted from a source of light of a luminous intensity of about 100 to 1500 mW/cm$^2$ in a wavelength region of about 360 to 500 nm (main absorption region of the α-diketone compound) from a distance of about 0 to about 10 mm. In a dental clinic, for example, the composite resin blended with the photopolymerization initiator is filled in a cavity of a tooth to be restored and is molded in the form of the tooth, and is cured by polymerization by being irradiated with the active light by using a special light irradiator to thereby restore the tooth. Further, a dental technician applies the composite resin onto a plaster model in the form of a tooth that is to be restored, and cures it by polymerization by the irradiation with the light. Then, a dentist adheres the thus obtained cured body to the tooth by using a dental adhesive to restore the tooth (see, for example, "Basics of the Photopolymerizable Composite Resin and Clinics", Hiroyasu Hosoda, Nihon Shika Shuppan Co., Feb. 10, 1986, pp. 9–20, Prior Art (A)).

However, when a combination of the α-diketone compound and the tertiary amine compound is used as the photopolymerization initiator, the viscosity of the composite resin (paste) increases while it is being filled or applied, making it difficult to carry out the operation.

That is, the operation for filling or applying the paste must be conducted under the illumination of incandescent light such as dental light for illuminating the oral cavity or room light such as fluorescent lamp (this kind of light is called environmental light) to make sure the shape of the paste and the color tone of the cured body obtained by polymerizing the paste. In general, the environmental light is adjusted to be about 500 to 10000 luxes for easy watching. The luminous intensity of environmental light over a range of 360 to 500 nm, which is a chief absorption region of the α-diketone compound is not larger than 1 mW/cm$^2$ though it may vary depending upon the source of light, which is several percent of the active light at the greatest. However, the polymerization initiator of a combination of the α-diketone compound and the tertiary amine compound exhibits a favorable polymerization activity for the light of visible region. Due to its good polymerization activity, therefore, the polymerization initiator sensitively reacts even to the environmental light and initiates curing. Therefore, if the operation of filling or application is conducted under the illumination of environmental light, the high polymerization activity turns into a disadvantage; i.e., the curing of the polymerization initiator proceeds to arouse the problems described above.

The phenomenon of an increase in the viscosity of the paste during the filling or application operation can be avoided by decreasing the amount of addition of the photopolymerization initiator or by the addition of a polymerization inhibitor in slightly large amounts. When this method is applied, however, the curing does not take place to a sufficient degree despite of the irradiation with the active light for a period of time same as that of the prior art, arousing such problems that the cured body that is obtained exhibits a decreased strength and that unpolymerized monomer remains in large amounts near the surface of the cured body. To effect the curing by polymerization to a sufficient degree, therefore, the time for irradiation with the active light must be lengthened. In many cases, however, the above composite resin is used in the oral cavity of a patient, and lengthening the irradiation time not only prolongs the operation time but also causes an increased burden to the patient. It has, therefore, been desired to shorten the irradiation time (curing time).

Even with the composite resin (paste) featuring improved stability against the environmental light as a result of decreasing the amount of addition of the photopolymerization initiator, it is allowed to shorten the curing time or to increase the strength of the cured body by increasing the luminous intensity of the irradiated active light. However, an increase in the luminous intensity requires an increase in the amount of energy correspondingly. Besides, too intense light even though it is visible light causes disturbance to the human body and, particularly, to the eyes. In general, further, the source of light emitting a highly intense light also generates the heat in large amounts which may damage the human body (in recent years, it is a trend to lower the energy of the source of active light, and there have been widely used light irradiators employing a laser diode or the like to emit the light of an intensity of about 20 to 100 mW/cm$^2$). That is, with the method of decreasing the amount of addition of the photopolymerization initiator, it is not allowed to shorten the curing time or to increase the strength of the cured body when there is used the light irradiator such as the laser diode, and it is difficult to effect the curing by polymerization quickly and to a sufficient degree without giving burden to the patient.

With the composite resin blended with the conventional photopolymerization initiator, as described above, it is not possible to enhance the stability against the environmental light without impairing the reaction activity for the active light. Namely, there has not yet been provided a composite resin having such properties that the curing does not take place with the weak light such as the environmental light and that the curing quickly takes place when it is irradiated with an intense light by using a dental irradiator.

In order to solve the above problems, a variety of photopolymerization initiators have been studied in addition to the combination of the α-diketone compound and the tertiary amine compound, as represented by, for example, a photocurable dental material comprising a (meth)acrylate polymerizable monomer, an acylphosphine oxide polymerization initiator and an amine compound (e.g., Japanese Unexamined Patent Publication (Kokai) No. 2000-16910 (prior art B)).

This dental material has a sufficiently high stability against the environmental light and exhibits high cured body properties, but requires the irradiation time for curing comparable to that of the conventional photocurable dental materials, and does not still satisfy the requirement of shortening the curing time.

It has further been known to use an aryl iodonium salt, a photo-sensitizing agent and an electron donor as polymerization initiator components (see, for example, U.S. Pat. No. 5,545,676 (prior art C)).

The composite resin containing the above polymerization initiator components can be cured by polymerization by being irradiated with the active light for a period of time that is shortened as compared to that of the conventional counterparts. However, the degree of shortening is not sufficient, and it has been desired to further shorten the time for irradiation with the active light (time for curing by polymerization). When the above photopolymerization initiator is used, further, there is seen no great improvement in the stability against the environment.

On the other hand, an s-triazine compound having a trihalomethyl group as a substituent is a compound that generates acid upon the irradiation with light, and has heretofore been used as a polymerization initiator for the photo-cationic polymerization. In recent years, however, the above s-triazine compound has been used as a radical polymerization initiator in combination with other components. For example, there has been proposed a radical polymerization initiator comprising a photo acid generator such as the above s-triazine compound, an aryl borate compound and a pigment that absorbs visible light (see, for example, U.S. Pat. Nos. 4,950,581 and 574,451 (prior arts D and E)).

In these photopolymerization initiators, the photo acid generator is decomposed by the irradiation with light to generate an acid which, then, decomposes the aryl borate compound to form active radical species that initiate the polymerization. The active radical species produced by the disintegration of the aryl borate compound offer such advantages as a very high polymerizing activity, are little impaired by oxygen from being polymerized as compared with the conventional radical polymerization initiators, cured within a short period of time, exhibit a sufficiently high activity even for the weak light, and are very useful as an adhesive for dental use.

Conversely, however, a sufficiently high activity for the weak light means that the stability is low against the environmental light. Therefore, it is not so desirable to use the above photopolymerization initiator for the dental composite resins.

It has further been proposed to use the s-triazine compound having the trihalomethyl group which is a substituent as the photopolymerization initiator in the addition polymerization compositions in combination with a photo-sensitizing compound and an electron donor compound (see, for example, EP 0369645 (prior art F)).

The above photopolymerization initiator has such advantages as a high polymerization activity and a high curing rate. According to the study conducted by the present inventors, however, the photopolymerizable composition blended with the above photopolymerization initiator exhibits a very high curing rate when there is used an irradiator equipped with a halogen lamp, but does not exhibit a favorable curing rate when there is used an irradiator equipped with a laser diode or a xenon lamp. Therefore, the irradiator is limited to the halogen lamp. Further, the above photopolymerizable composition has a defect in that the polymerization activity drops with the passage of time when it is preserved at a relatively high temperature of about 50° C. The dental materials are, in many cases, transported to dental clinics by using a passenger car. In the summer time, however, the temperature inside the vehicle often exceeds 50° C. Even if the temperature does not exceed 50° C., it is expected that the polymerization activity similarly drops when preserved for extended periods of time.

SUMMARY OF THE INVENTION

It is therefore an object of the present invention to provide a novel photopolymerization initiator which exhibits a high stability against the weak light such as the environmental light (intensity over 360 to 500 nm of smaller than 1 mW/cm$^2$), which is-completely cured within a very short period of time upon the irradiation with an intense light (intensity of not smaller than about 20 mW/cm$^2$ over the above wavelength region) emitted from the irradiator such as a halogen lamp, a xenon lamp or a laser diode, which forms a cured body having favorable properties, which exhibits excellent preservation stability and which can be effectively applied to the dental composite resins.

In order to solve the above problems, the present inventors have conducted keen study, and have discovered the fact that a photopolymerization initiator comprising an s-triazine compound having a trihalomethyl group as a substitutent, an α-diketone compound and an amine compound, exhibits improved sensitivity for the irradiator equipped with the halogen lamp, xenon lamp or laser diode (improved sensitivity for the active light) and is cured at an increased rate, when an aromatic amine compound and an aliphatic amine compound are used in combination as the amine compound. It was further discovered that owing to an increase in the curing rate, the polymerization activity (curing rate) is accomplished to a degree comparable to that of the prior art even when the amount of the α-diketone compound is decrease and that owing to a decrease in the amount of the α-diketone compound, the stability against the environmental light can be improved while maintaining the polymerization activity for the active light. The inventors have further discovered that the preservation stability is improved by the use of a particular amine compound or a particular s-triazine compound, and have thus completed the invention.

According to the present invention, there is provided a photopolymerization initiator comprising (A) an α-diketone compound, (B) an amine compound and (C) an s-triazine compound having a trihalomethyl group as a substituent, the amine compound (B) containing (B1) an aliphatic amine compound and (B2) an aromatic amine compound.

According to the present invention, further, there is provided a dental photopolymerizable composition blended with the above photopolymerization initiator.

According to the present invention, further, there is provided a photopolymerizable dental composite resin of the one-paste type containing the above photopolymerization initiator, a radically polymerizable monomer without acid group (D) and an inorganic filler (E).

As compared to the conventional known photopolymerization initiators, the photopolymerization initiator of the present invention has a high stability against the environmental light (weak light) when it has the same curing rate for the active light (intense light) or enables the curing by polymerization to be completed very quickly when it has the same stability against the environmental light. By using the aromatic amine compound and the aliphatic amine compound in combination as the amine compound, further, the photopolymerization initiator exhibits high polymerization activity irrespective of the kind of the source of light and accomplishes the curing within short periods of time. By using an aliphatic amine substituted with an electron attractive group, and a particular aromatic amine or a triazine compound having, as a substituent, an organic group with an unsaturated bond that is capable of conjugating with a triazine ring, further, it is allowed to obtain a favorable preservation stability without almost losing the polymerization activity even after preserved at high temperatures for extended periods of time. Besides, the obtained cured body exhibits a high mechanical strength, and can be particularly preferably used as a photopolymerizable composite resin which is a dental filling material.

DETAILED DESCRIPTION OF THE INVENTION (A) α-Diketone Compounds

In the photopolymerization initiator of the present invention, the α-diketone compound which is the component (A) may be any known compound without limitation. Its concrete examples include camphorquinones such as camphorquinone, camphorquinonecarboxylic acid and camphorquinonesulfonic acid; and diacetyl, acetylbenzoyl, 2,3-pentadione, 2,3-octadione, 9,10-phenanthrenequinone, and acenaphthenequinone.

The α-diketone compound that is used may be suitably selected depending upon the wavelength and intensity of light used for the polymerization, time for irradiating the light, or the kinds and amounts of other components that are used in combination. The α-diketone compound may be used in a single kind or being mixed together in two or more kinds. Among them, it is desired that the α-diketone compound has a maximum absorption wavelength in the region of visible light from the standpoint of dental use. In general, camphorquinones are desirably used and, particularly, the camphorquinone is used. The amount of the α-diketone that is used differs depending upon the kinds of other components to be used in combination or the kinds of the polymerizable monomers to be photopolymerized. Usually, however, the α-diketone is made present in the photopolymerization initiator in amounts in a range of 0.01 to 10 parts by mass and, particularly, 0.03 to 5 parts by mass per 100 parts by mass of the polymerizable monomers. Namely, the photopolymerization initiator of the present invention is contained in the polymerizable composition which contains the polymerizable monomers in such an amount that the amount of the α-diketone lies within the above range. The curing time with the active light shortens with an increase in the amount of the α-diketone. On the other hand, the stability against the environmental light becomes excellent as the amount thereof decreases.

(B) Amine Compounds

As the amine compound which is the component (B), there are used an aliphatic amine compound (B1) and an aromatic amine compound (B2) in combination.

(B1) Aliphatic Amine Compounds

As the aliphatic amine compound (B1), there can be used any one of a primary amine, a secondary amine or a tertiary amine. However, the primary and secondary amines are highly volatile and generate odor. For the dental use, therefore, there is preferably used the tertiary amine free of such problems.

Among the tertiary amines, further, it is desired to use the compound having a tertiary amino group in which three saturated aliphatic groups are bonded to a nitrogen atom, at least two of the saturated aliphatic groups having electron attractive groups as substituents, from the standpoint of further improving the preservation stability. The tertiary amine tends to exhibit a higher polymerization activity than those of the primary amine and the secondary amine. Use of the compound (aliphatic tertiary amine) having the above particular tertiary amino group (aliphatic tertiary amino group) makes it possible to obtain a higher polymerization activity and, hence, to obtain further excellent preservation stability.

The electron attractive group in the above aliphatic tertiary amino group works to attract the electron from the carbon atom of the saturated aliphatic group to which the group is bonded, and may be any known electron attractive group. From the standpoint of chemical stability, however, the electron attractive group is preferably a hydroxyl group; an aryl group such as phenyl group or naphthyl group; an unsaturated aliphatic group such as ethenyl group (vinyl group), 1-propenyl group or ethynyl group; a fluorine atom; an alkoxyl group; a carbonyl group; a carbonyloxy group; or a cyano group. Among them, it is desired to use an aryl group, an unsaturated aliphatic group or a hydroxyl group from the standpoint of stability of the compound, easy synthesis and excellent solubility in the polymerizable monomers. Particularly preferably, the hydroxyl group is used.

There is no particular limitation on the saturated aliphatic group to which the electron attractive group is bonded, and the saturated aliphatic group may be any one of the straight chain, branch or cyclic form. From the standpoint of easy synthesis and availability, however, the saturated aliphatic group is the one of a straight chain or a branched chain having 1 to 6 carbon atoms such as a methyl group, an ethyl group, a propyl group or a butyl group. There is no particular limitation, either, on the position or the number to where the electron attractive group is substituted (bonded). However, the preservation stability is more improved as the electron attractive group is bonded to the carbon atom close to the nitrogen atom of the amino group. It is desired that the electron attractive group is bonded to a carbon atom bonded to the nitrogen atom (first position of the saturated aliphatic group) or is bonded to a neighboring carbon atom (second position).

Concrete examples of the saturated aliphatic group having the electron attractive group as a substituent include those having a hydroxyl group (electron attractive group) such as 2-hydroxyethyl group, 2-hydroxypropyl group, 2-hydroxybutyl group, and 2,3-dihydroxypropyl group; those having an unsaturated aliphatic group (electron attractive group) such as allyl group (ethenylmethyl group), 2-propynyl group (ethynylmethyl group) and 2-butenyl group; and those having an aryl group (electron attractive group) such as benzyl group, etc.

Namely, in the present invention, the aliphatic tertiary amine preferably used as the aliphatic amine compound (B1) has a tertiary amino group in which three saturated aliphatic groups are bonded to a nitrogen atom. The tertiary amino groups can roughly be divided into those of the following three types (a) to (c). (a) Those in which none of the three saturated aliphatic groups bonded to the nitrogen atom have the electron attractive group as a substituent.

Examples of the tertiary amines having the tertiary amino group of this type (a) include triethylamine and tributylamine. (b) Those in which one of the three saturated aliphatic groups bonded to the nitrogen atom has the electron attractive group as a substituent (two of them do not have the electron attractive group as the substituent).

Examples of the tertiary amines having the tertiary amino group of this type (b) include dimethylaminoethanol, diethylaminoethanol, dimethylaminopropanol, N,N-dimethylaminoethyl methacrylate and-N,N-diethylaminoethyl methacrylate. (c) Those in which two or more of the three saturated aliphatic groups bonded to the nitrogen atom have the electron attractive groups as substituents.

Examples of the tertiary amines having the tertiary amino groups of this type (c) include those having two saturated aliphatic groups substituted with electron attractive groups, such as N-methyldiethaholamine, N-ethyldiethanolamine, N-propyldiethanolamine, N-ethyldiallylamine, and N-ethyldibenzylamine, etc., and those having three saturated aliphatic groups substituted with electron attractive groups, such as triethanolamine, tri(isopropanol)amine, tri(2-hydroxybutyl)amine, triallylamine and tribenzylamine.

In the present invention as described already, the tertiary amine having the tertiary amino group of the type (c) is most desirably used. As demonstrated in Working Examples appearing later, therefore, this further greatly improves the preservation stability compared to those of using the tertiary amine having the tertiary amino group of the type (a) having no saturated aliphatic group substituted with the electron attractive group or those of using the tertiary amine having the tertiary amino group of the type (b) having one saturated aliphatic group substituted with the electron attractive group.

(B2) Aromatic Amine Compounds

The aromatic amine compound which is the component (B2) used in combination with the above aliphatic amine compound (B1) may be an amine compound in which at least one of the organic groups bonded to the nitrogen atom of the amino group is an aromatic group, and any known aromatic amine compound can be used without any limitation. From the standpoint of high polymerization activity, lowly volatile property and hence small odor and easy availability, however, it is desired to use an amine compound (aromatic tertiary amine) having an aromatic tertiary amino group in which one aromatic group and two aliphatic groups are bonded to the nitrogen atom. A representative aromatic tertiary amine is expressed by the following general formula (1),

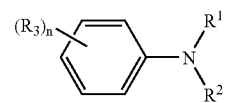

wherein $R^1$ and $R^2$ are, independently from each other, alkyl groups, $R^3$ is an alkyl group, an aryl group, an alkenyl group, an alkoxy group or an alkyloxycarbonyl group, n is an integer of 0 to 5 and, when n is not smaller than 2, a plurality of $R^3$ may be the same or different.

The alkyl group, preferably, has 1 to 6 carbon atoms, and is a methyl group, an ethyl group, an n-propyl group, an i-propyl group, an n-butyl group, or an n-hexyl group. Further, the alkyl group may be a substituted alkyl group having a substituent, as a matter of course. As the substituted alkyl group, there can be exemplified halogen-substituted alkyl groups such as fluoromethyl group and 2-fluoroethyl group; and hydroxyl group-substituted alkyl groups such as 2-hydroxyethyl group, etc.

The aromatic amine compound may have any substituent of aryl group, alkenyl group, alkoxy group or alkyloxycarbonyl group. As the aryl group, there can be exemplified a phenyl group, a p-methoxyphenyl group, a p-methylthiophenyl group, a p-chlorophenyl group or a 4-biphenylyl group having 6 to 12 carbon atoms. As the alkenyl group, there can be exemplified a vinyl group, an allyl group or a 2-phenylethenyl group having 2 to 12 carbon atoms. As the alkoxy group, there can be exemplified a methoxy group, an ethoxy group or a butoxy group having 1 to 10 carbon atoms. As the alkyloxycarbonyl group, there can be exemplified a methoxycarbonyl group, an ethoxycarbonyl group, a butoxycarbonyl group, an amyloxycarbonyl group and an isoamyloxycabonyl group having 2 to 10 carbon atoms in the alkyloxy group portion.

In the aromatic tertiary amine of the above general formula (1), it is desired that the groups $R^1$ and $R^2$ are alkyl groups having 1 to 6 carbon atoms and, particularly, unsubstituted alkyl groups (e.g., methyl groups, ethyl groups, n-propyl groups) having 1 to 3 carbon atoms, or 2-hydroxyethyl groups.

It is further desired that when n=1, the group $R^3$ is bonded at the para-position and, particularly, the group $R^3$ is an alkyloxycarbonyl group. Superior preservation stability is obtained when the aromatic amine having an aromatic group substituted with the alkyloxycarbonyl group is used in combination with the aliphatic amine compound which is the component (B1).

Concrete examples of the tertiary amine having the aromatic group in which the alkyloxycarbonyl group (group $R^3$) is bonded to the para-position include methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate, and propyl p-diethylaminobenzoate.

When the groups $R^3$ are bonded in a number of two to three, it is desired that the bonding positions are ortho-positions and/or the para-positions. With the plurality of groups $R^3$ being coupled to the ortho-positions and the para-positions, the cured product exhibits favorable stability against the sunlight. It is particularly desired that the groups $R^3$ are bonded to all ortho-positions or para-positions.

Concrete examples of the tertiary amine having an aromatic group in which two to three groups $R^3$ are bonded to the ortho-positions and/or the para-positions, include N,N-2,4,6-pentylmethylamiline, N,N,2,4-tetramethylaniline and N,N-diethyl-2,4,6-trimethylaniline.

As the other aromatic amine represented by the general formula (1), further, there can be exemplified N,N-dimethylaniline, N,N-dibenzylaniline, N,N-dimethyl-p-toluidine, N,N-diethyl-p-toluidine and N,N-di(β-hydroxyethyl)-p-toluidine.

In the present invention, the amount of the amine compound (total amount of the component (B1) and of the component (B2))which is the component (B) comprising the aliphatic amine compound (B1) and the aromatic amine compound (B2), is, usually, in a range of 10 to 1000 parts by mass and, particularly, 50 to 500 parts by mass per 100 parts by mass of the α-diketone component which is the component (A). More preferably, the amine compound which is the component (B) is used in an amount of 0.01 to 10 parts by mass and, particularly, 0.02 to 5 parts by mass per 100 parts by mass of the polymerizable monomers in the polymerizable composition blended with the photopolymerization initiator.

As the aliphatic amine compound (B1) and the aromatic amine compound (B2), further, there can be used the compounds exemplified above in one kind or in a combination of two or more kinds. Here, it is desired that the two compounds are used in combination at such a mass ratio (B1):(B2) of 3:97 to 97:3, preferably, 10:90 to 75:25 and, particularly, 20:80 to 60:40.

(C) s-Triazine Compounds Substituted with the Trihalomethyl Substituent

The photopolymerization initiator of the present invention uses the s-triazine compound (hereinafter often simply referred to as triazine compound) having a trihalomethyl group as a substituent together with the above-mentioned components (A) and (B).

As the triazine compound of the invention, there can be used any known compound without limitation provided it is an s-triazine compound having at least one trihalomethyl group such as trichloromethyl group or tribromomethyl group. A particularly desired triazine compound is expressed by the following general formula (2),

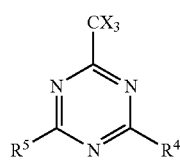

(2)

wherein $R^4$ and $R^5$ are hydroxyl groups, organic groups having an unsaturated bond that is capable of conjugating with the triazine ring, or are alkyl groups or alkoxy groups, and X is a halogen atom.

In the above general formula (2), the halogen atom denoted by X may be any one of chlorine, bromine or iodine but is, usually, chlorine. Therefore, the substituent ($CX_3$) bonded to the triazine ring is, usually, a trichloromethyl group.

$R^4$ and $R^5$ may be hydroxyl groups, organic groups having an unsaturated bond that is capable of conjugating with the triazine ring, alkyl groups or alkoxy groups. To enhance the preservation stability, however, it is desired that at least either $R^4$ or $R^5$ is an organic group having an unsaturated bond that is capable of conjugating with the triazine ring.

On the other hand, good polymerization activity is obtained when at least either $R^4$ or $R^5$ is a halogen-substituted alkyl group, and particularly good polymerization activity is obtained when both of them are halogen-substituted alkyl groups.

As the organic group bonded through the unsaturated bond that is capable of conjugating with the triazine ring, there can be used any known organic group. Preferably, however, there is used an organic group having 2 to 30 carbon atoms and, particularly, 2 to 14 carbon atoms. Concrete examples of the organic group include aryl groups having 6 to 14 carbon atoms, such as phenyl group, methoxyphenyl group, p-methylthiophenyl group, p-chlorophenyl group, 4-biphenyl group, naphthyl group and 4-methoxy-1-naphthyl group; and alkenyl groups having 2 to 14 carbon atoms, such as vinyl group, 2-phenylethenyl group, and 2-(substituted phenyl)ethenyl group. As the substituent having the substituted phenyl group, there can be exemplified alkyl groups having 1 to 6 carbon atoms, such as methyl group, ethyl group and propyl group; alkoxy groups having 1 to 6 carbon atoms, such as methoxy group, ethoxy group, and propoxy group; alkylthio groups having 1 to 6 carbon atoms, such as methylthio group, ethylthio group and propylthio group; phenyl group; and halogen atom.

Further, the alkyl groups and alkoxy groups denoted by $R^4$ and $R^5$ may have a substituent. The alkyl group preferably has 1 to 10 carbon atoms, and may be an unsubstituted alkyl group, such as methyl group, ethyl group, n-propyl group, i-propyl group, n-butyl group or n-hexyl group; or a halogen-substituted alkyl group, such as trichloromethyl group, tribromomethyl group, or α, α, β-trichloroethyl group. The alkoxy group preferably has 1 to 10 carbon atoms, and may be unsubstituted alkoxy group such as methoxy group, ethoxy group or butoxy group; or alkoxy group substituted with an amino group, such as 2-{N,N-bis(2-hydroxyethyl) amino}ethoxy group, 2-{N-hydroxyethyl-N-ethylamino}ethoxy group, 2-{N-hydroxyethyl-N-methylamino}ethoxy group, or 2-{N,N-diallylamino}ethoxy group.

Concretely described below are the examples of the s-triazine compound substituted with the trihalomethyl group represented by the above general formula (2), i.e., 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-(α,α,β-trichloroethyl)-4,6-bis(trichloromethyl)-s-triazine, 2-styryl-4,6-bis(trichloromethyl)-s-triazine, 2-[2-(p-methoxyphenyl) ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl) ethenyl]-4,6-bis(trichloromethyl)-s-triazine, 2-[2-(3,4,5-trimethoxyphenyl)ethenyl]-4,6-bis(trichloro-methyl)-s-triazine, 2-(1-naphthyl)-4,6-bis(trichloromethyl)-s-triazine, 2-(4-biphenylyl)-4,6-bis(trichloromethyl)-s-triazine, 2-[2-

{N,N-bis(2-hydroxyethyl)amino}ethoxy]-4,6-bis(tri-chloromethyl)-s-triazine, 2-[2-{N-hydroxyethyl-N-ethylamino}ethoxy]-4,6-bis(tri-chloromethyl)-s-triazine, 2-[2-{N-hydroxyethyl-N-methylamino}ethoxy]-4,6-bis(trichloromethyl)-s-triazine, 2-[2-{N,N-diallylamino}ethoxy]-4,6-bis(trichloromethyl)-s-triazine, 4,6-bis(trichloromethyl)-1,3,5-triazine-2(1H)-one, 4,6-bis(tribromomethyl)-1,3,5-triazine-2(1H)-one, 4-phenyl-6-trichloromethyl-1,3,5-triazine-2(1H)-one, 4-phenyl-6-tribromomethyl-1,3,5-triazine-2(1H)-one, 4-(p-chlorophenyl)-6-trichloromethyl-1,3,5-triazine-2(1H)-one, 4-(m-methoxyphenyl)-6-trichloromethyl-1,3,5-triazine-2(1H)-one, 4-(p-methoxyphenyl)-6-trichloromethyl-1,3,5-triazine-2(1H)-one, 4-phenylethenyl-6-trichloromethyl-1,3,5-triazine-2(1H)-one, 4-phenylethenyl-6-tribromomethyl-1,3,5-triazine-2(1H)-one, 4-(4-biphenylyl)-6-trichloromethyl-1,3,5-triazine-2(1H)-one, and 4-methoxy-6-trichloromethyl-1,3,5-triazine-2(1H)-one.

In the above-mentioned triazine compounds, the compound in which $R^3$ or $R^4$ is a hydroxyl group, in many cases, exists in the form of a 1,3,5-triazine-2(1H)-one compound expressed by the following general formula (3) due to the isomerization reaction. Therefore, the above compound is named as 1,3,5-triazine-2(1H)-one compound.

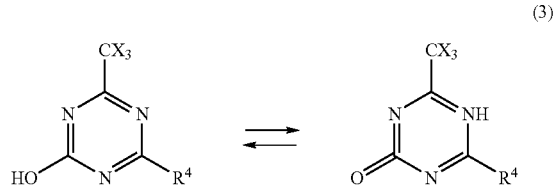

(3)

Among the triazine compounds exemplified above, particularly preferred compounds are 2,4,6-tris(trichloromethyl)-s-triazine, 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine. It is desired to use the above triazine compounds from the standpoint of obtaining a polymerization initiator having excellent stability against the sunlight and obtaining a cured body having excellent color tone.

The above triazine compounds may be used in one kind or being mixed together in two or more kinds. The amount of addition thereof is usually in a range of 5 to 1000 parts by mass and, more preferably, 30 to 500 parts by mass per 100 parts by mass of the α-diketone compound which is the component (A). Desirably, the triazine compound which is the component (C) is used in an amount of 0.005 to 10 parts by mass and, particularly, 0.03 to 5 parts by mass per 100 parts by mass of the polymerizable monomers in the polymerizable composition blended with the photopolymerization initiator. (Use of the photopolymerization initiator)

The photopolymerization initiator of the present invention is used for polymerizing the polymerizable monomers. There can be used any polymerization initiator for the photopolymerizable compositions without limitation. For example, it can be used as a polymerizable composition in combination with any polymerizable monomers. Among them, it is desired to use it as the polymerization initiator for the photopolymerizable dental composite resins. As described already, the composite resin must satisfy the requirements of excellent stability against the environmental light and curing rate. Besides, the composite resin is used in small amounts each time, and is preserved for extended periods of time after it is produced and must, hence, satisfy the requirement of preservation stability. Use of the photopolymerization initiator of the present invention makes it possible to satisfy all of such requirements.

The photopolymerizable dental composite resin is a material used for restoring a tooth that is changed by caries, abrasion, etc., and, usually, comprises a (meth)acrylate polymerizable monomer and an inorganic filler as chief components, and is blended with a photopolymerization initiator for effecting the curing by polymerization upon the irradiation with visible light. In order to improve the operability, further, there are, in many cases, used the materials of the one-paste type that need not be mixed at the time of use.

Described below in further detail is a photopolymerizable dental composite resin which is a representative example of the photopolymerizable composition using the photopolymerization initiator of the present invention.

The composite resin contains a radically polymerizable monomer (D) and an inorganic filler (E) in addition to the photopolymerization initiator.

The amine compound {aliphatic amine (B1) and aromatic amine (B2)} which is the component (B) of the photopolymerization initiator of the present invention reacts with an acid to form a salt, and tends to lose the polymerization activity. It is, therefore, desired not to blend the polymerizable monomers having acidic groups, such as (meth)acrylic acid, p-(meth)acryloyloxybenzoic acid, 10-methacryloyloxydecamethylenemalonic acid, and 2-hydroxyethylphenylhydrogen phosphate, except when they are unavoidably infiltrated. When their amounts are those of generally existing impurities, the amine compound is used in large amounts to maintain the polymerization activity. In this case, the preferred blending amount of the amine compound is for removing the components that are neutralized with the acid. In general, the aliphatic amine exhibits higher activity as a base than the aromatic amine, and tends to be neutralized with the acid. It is therefore recommended to calculate the amount of the amine compound all as the aliphatic amine which is the component (B1) that is consumed in the neutralization reaction.

A preferred blending amount of the photopolymerization initiator of the present invention in the dental composite resin is such that the amount of the component (A) in the photopolymerization initiator is 0.01 to 10 parts by mass and, particularly, 0.03 to 5 parts by mass per 100 parts by mass of the radically polymerizable monomer (D). In general, the amount of the photopolymerization initiator (total amount of the components (A) to (C)) is in the range of 0.01 to 20 parts by mass, preferably, 0.05 to 10 parts by mass and, particularly, preferably, 0.1 to 3 parts by mass per 100 parts by mass of the polymerizable monomer.

Radically Polymerizable Monomer (D)

As the polymerizable monomer (D), there is preferably used a (meth)acrylate polymerizable monomer without acidic group (sulfonic acid group, carboxyl group, phosphoric acid residue, etc.) from the standpoint of curing rate, mechanical properties of the cured body, water resistance, color resistance and preservation stability. Particularly preferably, there is used a polyfunctional (meth)acrylate polymerizable monomer having a plurality of polymerizable functional groups. Any known polyfunctional (meth)acrylate polymerizable monomer can be used without limitation. Preferred examples that are generally used are those described in (I) to (III) below.

(I) Bifunctional Polymerizable Monomers (i) Aromatic Compound Type 2,2-bis[4-(3-methacryloyloxy-2-hydroxypropoxy)phenyl]propane, 2,2-bis(4-methacryloyloxyphenyl)propane, 2,2-bis(4-methacryloyloxypolyethoxyphenyl)propane, 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2(4-methacryloyloxydiethoxyphenyl)-2(4-methacryloyloxytriethoxyphenyl)propane, 2(4-methacryloyloxydipropoxyphenyl)-2-(4-methacryloyloxytriethoxyphenyl)propane, 2,2-bis(4-methacryloyloxypropoxyphenyl)propane, 2,2-bis(4-methacryloyloxyisopropoxyphenyl)propane, acrylates corresponding to the above various methacrylates, and diadducts obtained by the addition of an OH group-containing vinyl monomer and a diisocyanate compound having an aromatic group.

As the OH group-containing vinyl monomer, there can be exemplified methacrylates such as 2-hydroxyethyl methacrylate, 2-hydroxypropyl methacrylate, 3-chloro-2-hydroxypropyl methacrylate, and acrylates corresponding to these methacrylates. As the diisocyanate, there can be exemplified diisocyanatemethylbenzene and 4,4'-diphenylmethanediisocyanate.

(ii) Aliphatic Compound Type 1,2-bis(3-methacryloyloxy-2-hydroxypropoxy)ethane; ethylene glycol dimethacrylate, diethylene glycol dimethacrylate, triethylene glycol dimethacrylate, tetraethylene glycol dimethacrylate, neopentyl glycol dimethacrylate, 1,3-butanediol dimethacrylate, 1,4-butanediol dimethacrylate, 1,6-hexanediol dimethacrylate, and acrylates corresponding to these methacrylates; and diadducts obtained by the addition of an OH group-containing vinyl monomer and an aliphatic diisocyanate compound.

As the OH group-containing vinyl monomer, there can be exemplified the ones which are the same as those exemplified above. As the aliphatic diisocyanate compound, there can be exemplified hexamethylene diisocyanate, trimethylhexamethylene diisocyanate, diisocyanatemethylcyclohexane, isophorone diisocyanate and methylenebis(4-cyclohexylisocyanate).

(II) Trifunctional Polymerizable Monomers

Trimethylolpropane trimethacrylate, trimethylolethane trimethacrylate, pentaerythritol trimethacrylate, and trimethylolmethane trimethacrylate; and acrylates corresponding to these methacrylates.

(III) Tetrafunctional Polymerizable Monomers

Pentaerythritol tetramethacrylate; Pentaerithritol tetraacrylate; and Diadducts obtained from the addition of the diisocyanate compound and the glycidol dimethacrylate.

As the diisocyanate compound, there can be exemplified diisocyanatemethylbenzene, diisocyanatemethylcyclohexane, isophoronediisocyanate, hexamethylenediisocyanate, trimethylhexamethylenediisocyanate, methylenebis(4-cyclohexylisocyanate), 4,4-diphenylmethanediisocyanate, and tolylene-2,4-diisocyanate.

As required, there may be used a plurality of kinds of polyfunctional (meth)acrylate monomers.

As required, further, there may be used polymerizable monomers other than the monofunctional (meth)acrylate monomers and the polyfunctional (meth)acrylate monomers. As the monofunctional (meth)acrylate monomer, there can be exemplified methyl(meth)acrylate, ethyl(meth)acrylate, isopropyl(meth)acrylate, hydroxyethyl(meth)acrylate, tetrahydrofurfuryl(meth)acrylate and glycidyl(meth)acrylate.

Inorganic Fillers (E)

There can be used any known inorganic filler that has been used without limitation for the dental composite resins. Representative examples of the inorganic filler include metal oxides such as quartz, silica, alumina, silica-titania, silica-zirconia, lanthanum glass, barium glass and strontium glass. As required, further, there can be blended a known cation-eluting inorganic filler that is used for the dental applications, such as silicate glass and fluoroaluminosilicate glass, which may be used in one kind or being mixed together in two or more kinds.

Further, the polymerizable monomer may be added in advance to the inorganic filler to obtain a paste thereof, which is, then, polymerized and pulverized to obtain a granular organic/inorganic composite filler.

There is no particular limitation on the particle size of the filler, and there is suitably used, depending on an object, a filler having an average particle size of 0.01 µm to 100 µm (particularly, preferably, 0.01 to 5 µm) that is usually used as a dental material. There is no limitation, either, on the refractive index of the filler. That is, the inorganic filler having a refractive index over a range of 1.4 to 1.7 that is usually used for the dental applications can be used without limitation, and the refractive index may be suitably set depending upon the object. There may be used in combination a plurality of inorganic fillers having different particle sizes and different refractive indexes.

Among the above-mentioned fillers, further, use of the spherical inorganic filler makes it possible to increase the surface gloss of the obtained cured body and to obtain an excellent dental composite resin.

It is desired that the inorganic filler is treated with a surface-treating agent as represented by a silane coupling agent from the standpoint of improving affinity to the polymerizable monomers and improving the mechanical strength and water resistance. The surface treatment may be conducted by a known method. As the silane coupling agent, there can be preferably used methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy)silane, γ-methacryloyloxypropyltrimethoxysilane, γ-chloropropyltrimethoxysilane, γ-glycidoxypropyltrimethoxysilane and hexamethyldisilazane.

The ratio of the filler may be suitably determined depending upon the object by taking into consideration the viscosity (operability) of when it is mixed into the polymerizable monomers and the mechanical properties of the cured body. Usually, however, the filler is used in a range of 50 to 1500 parts by mass and, preferably, 70 to 1000 parts by mass per 100 parts by mass of the polymerizable monomers (D).

Other Components

To achieve the color tone of the teeth, there may be added a pigment, a fluorescent pigment, a dye and an ultraviolet-ray absorbing agent for preventing color changing due to ultraviolet rays, in addition to adding the above-mentioned components. There can be further added known additives as dental composite resin components within a range of not affecting the effect of the invention.

There is no particular limitation on the method of producing the photopolymerizable composite resin, and a known method may be employed for producing the photopolymerizable composite resin. Usually, the components to be blended are weighed by predetermined amounts and are kneaded together so as to become homogeneous under a light-shielding condition.

The photopolymerization initiator of the present invention is particularly preferably used for the photopolymerizable dental composite resin of the one-paste type, and can be used for any other applications as the photopolymerizable composition being mixed with the polymerizable monomers. Though there is no particular limitation, examples of use include dental adhesive, denture base material, photoresist material, printing plate material and hologram material. In these general applications, it is also allowable to mix and polymerize other polymerizable monomers than the above (meth)acrylate polymerizable monomers in addition to the above (meth)acrylate polymerizable monomers for easy polymerization, for adjusting the viscosity and for adjusting other properties. Examples of the other polymerizable monomers include fumaric acid esters such as monomethyl fumarate, diethyl fumarate and diphenyl fumarate; styrenes or α-methylstyrene derivatives, such as styrene, divinylbenzene, α-methylstyrene and α-methylstyrene dimer; and allyl compounds such as diallyl terephthalate, diallyl phthalate and diallyl diglycol carbonate. These polymerizable monomers may be used in one kind or in two or more kinds in combination.

Further, the photopolymerizable composition blended with the photopolymerization initiator of the present invention may be blended with other known polymerization initiators within a range of not impairing the effect of the invention. As the other polymerization initiator components, there can be used organic perioxides such as benzoyl peroxide and cumene hydroperoxide; +IV-valent or +V-valent vanadium compounds such as vanadium (IV) oxide acetyl acetonato and bis(maltolato)oxovanadium (IV); aryl borate compounds such as sodium tetraphenylborate, tetraphenylborate triethanolamine salt, tetraphenylborate dimethyl-p-toluidine salt, sodium tetrakis(p-fluorophenyl)borate, and sodium butyltri(p-fluorophenyl)borate; cumarin type dyes such as 3,3'-carbonylbis(7-diethylamino)cumarin and 7-hydroxy-4-methyl-cumarin; acylphosphineoxides such as bis (2,4,6-trimethylbenzoyl)-phenylphosphineoxide, bis(2,6-dimethoxybenzoyl)-2,4,4-trimethylpentylphosphin-oxide; benzoinalkyl ethers such as benzoinmethyl ether, benzoinethyl ether and benzoinpropyl ether; thioxanthone derivatives such as 2,4-diethoxythioxanthone, 2-chlorothioxanthone and methylthioxanthone; and benzophenone derivatives such as benzophenone, p,p'-bis(dimethylamino) benzophenone and p,p'-dimethoxybenzophenone. In order to obtain high stability against the environmental light, however, it is desired that the aryl borate compounds and the organic peroxides are used in amounts as small as possible. Further, dyes such as cumarin type dyes that are used in such large amounts as to act as polymerization initiators, seriously affect the color tone of the photopolymerizable composition, and cause the dental composite resin for which high aesthetic appearance is required to exhibit a color tone different from that of the teeth.

It is further allowable, depending upon the object, to add water, organic solvent or a viscosity-imparting agent to the photopolymerizable composition blended with the photopolymerization initiator of the present invention within a range in which they do not deteriorate the properties. As the organic solvent, there can be used hexane, heptane, octane, toluene, dichloromethan, methanol, ethanol or ethyl acetate. As the viscosity-imparting agent, there can be used a high molecular compound such as polyvinylpyrrolidone, carboxymethyl cellulose or polyvinyl alcohol, and highly dispersing silica.

To cure the photopolymerizable composition blended with the photopolymerizable initiator of the present invention, there may be used a known source of light which is the same as the one used for curing the α-diketone photopolymerization initiator. In order to draw the feature of the photopolymerization initiator of the present invention in that it remains relatively stable for the light of a low intensity but quickly cures upon the irradiation with the light having an intensity greater than a certain level, however, there can be used, without any limitation, a source of visible light, such as carbon arc, xenone lamp, metal halide lamp, tungsten lamp, LED, halogen lamp, helium-cadmium laser or argon laser. The irradiation time varies depending upon the wavelength and intensity of the source of light and upon the shape and material of the cured body, and may be determined in advance through experiment.

EXAMPLES

The invention will be described below more concretely by way of Working Examples to which only, however, the invention is in no way limited. Abbreviations of the compounds used in the following Examples and Comparative Examples (1) Abbreviations
(A) α-diketone
   CQ: camphorquinone
(B1) Aliphatic amine compounds
(B1-1) Compounds having two to three saturated aliphatic groups substituted with electron attractive groups.
   TEOA: triethanolamine
   EDEOA: N-ethyldiethanolamine
   MDEOA: N-methyldiethanolamine
   TAA: triallylamine
(B1-2) Compounds having only one saturated aliphatic group substituted with electron attractive group.
   DMEM: N,N-dimethylaminoethyl methacrylate
   DEEOA: N,N-diethylethanolamine
(B1-3) Compounds without having saturated aliphatic group substituted with electron attractive group.
   TEA: triethylamine
(B2) Aromatic amine compounds.
   DMBE: ethyl N,N-dimethyl p-benzoate
   DMBI: isoamyl N,N-dimethyl p-benzoate
   PEAT: N,N-diethyl p-toluidine
   DMPT: N,N-dimethyl p-toluidine
   PMAN: N,N,2,4,6-pentamethylaniline
(C) s-Triazine compound substituted with a trihalomethyl substituent.
   TCT: 2,4,6-tris(trichloromethyl)-s-triazine
   PBCT: 2-phenyl-4,6-bis(trichloromethyl)-s-triazine
   CBCT: 2-(p-chlorophenyl)-4,6-bis(trichloromethyl)-s-triazine
   MPBCT: 2-(p-methoxyphenyl)-4,6-bis(trichloromethyl)-s-triazine
   MNBCT: 2-(4-methoxy-1-naphthyl)-4,6-bis(trichloromethyl)-s-triazine
   PEBCT: 2-(2-phenylethenyl)-4,6-bis(trichloromethyl)-s-triazine
   MPBCT: 2-[2-(4-methoxyphenyl)ethenyl]-4,6-bis(trichloromethyl)-s-triazine BPBCT: 2-(4-biphenylyl)-4,6-bis(trichloromethyl)-s-triazine
(D) Polymerizable monomers.
  bis-GMA: 2,2-bis[4-(3-methacryloyloxy-2-hydroxypropyloxy)phenyl]propane
  D2.6E: compound represented by the following formula,

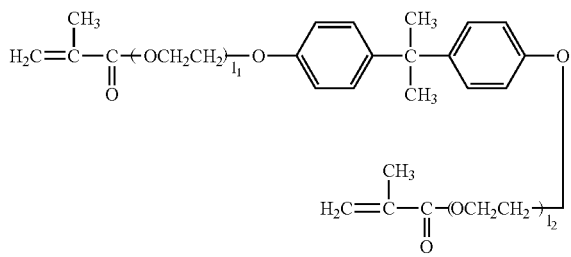

*A mixture having an average $(l_1+l_2)$ of 2.6.
  3G: triethylene glycol dimethacrylate
  UDMA: 1,6-bis(methacrylethyloxycarbonylamino) trimethylhexane
(E) Inorganic fillers.
  E-1: spherical silica-zirconia (γ-methacryloyloxypropyl trimethoxysilane of which the surfaces are treated, average particle size of 0.5 μm)
  E-2: spherical silica-zirconia (γ-methacryloyloxypropyl trimethoxysilane of which the surfaces are treated, average particle size of 0.2 μm)
  E-3: spherical silica-titania (γ-methacryloyloxypropyl trimethoxysilane of which the surfaces are treated, average particle size of 0.08 μm)
  E-4: the one obtained by dispersing above spherical silica-zirconia (E-2) in the polymerizable monomers of bis-GMA/3G=60/40 and followed by curing by polymerization and by milling (average particle size of 30 μm)
(F) Other components.
  HQME: hydroquinonemonomethyl ether
  BHT: 2,6-di-t-butyl-4-methylphenol
  DPI•BPh4: diphenyliodium•tetrahenyl borate Preparation of the photocurable composite resin and measurement of the curing properties (stability against the environmental light, curing time, hardness) and of the mechanical strength and preservation stability of the cured body, were carried out relying upon the methods described below.

(1) Preparation of the photo-curable composition:
Photopolymerization initiators, inorganic fillers and blending components were added in predetermined amounts to the polymerizable monomers, and were homogeneously mixed under red light and defoamed to prepare the photocurable composition.

(2) Intensity of irradiation light:
The intensity of light (mW/cm$^2$) on the surface irradiated was measured over the wavelengths of 360 to 500 nm by using UIT-101 manufactured by Ushio Denki Co.

(3-1) Curability by the irradiation with a laser diode:
A mold (the thickness of 1.5 mm) of a polytetrafluoroethylene having a hole of 7 mm in diameter was filled with a paste of a photo-curable composition, pressed with a polypropylene film, and a slide glass of a thickness of 2 mm was placed on the polypropylene film. The light was irradiated for 3 to 5 seconds in a state where the irradiation port of a dental light irradiator "LM" was in intimate contact with the slide glass. After irradiated with the light for a predetermined period of time, the cured body was taken out from the mold. The gel portion was removed from the cured body, and the diameter of the remaining cured body was measured to judge the curability.

Dental light irradiator "LM": LUX-O-MAX manufactured by
  Akeda Dental Co., light output density: 137 mW/cm$^2$, light intensity on the irradiated surface: 35 mW/cm$^2$, source of light: laser diode, port diameter of irradiation: 8 mm.

(3-2) Curability by the irradiation with a xenon lamp:
The diameter of the obtained cured body was measured by conducting the same operation as that of the measurement by using the laser diode with the exception of changing the dental light irradiator from "LM" into "A95" and setting the irradiation time to be 1 to 3 seconds.

Dental light irradiator "A95": Apolo 95E manufactured by
  DMD Co., light output density: 1370 mW/cm$^2$, light intensity on the irradiated surface could not be measured (very strong), irradiated for 3 seconds, source of light: xenon lamp, port diameter of irradiation: 8 mm.

(3-3) Curability by the irradiation with a halogen lamp.
A mold (the thickness of 1.0 mm) of a polytetrafluoroethylene having a hole of 6 mm in diameter was filled with a paste of a photo-curable composition, pressed with a polypropylene film, and was irradiated for 5 seconds, 10 seconds and 15 seconds maintaining an interval of 5 seconds in a state where the irradiation port of a dental light irradiator "TP" was in intimate contact with the polypropylene film. The cured bodies after the respective irradiation times were touched by hand to evaluate their hardness on the following basis.
  ○: Cured to a sufficient degree and is hard.
  Δ: Slightly cured and is in a soft gel-like state.
  ×: Not quite cured.

Dental light irradiator "TP": Tokuso Power Light manufactured by Tokuyama Dental Co., light output density: 700 mW/cm$^2$, light intensity on the irradiated surface: 640 to 650 mW/cm$^2$, source of light: halogen lamp, port diameter of irradiation: 8 mm.

(4) Hardness of the cured body (Vicker's hardness).
By using the above-mentioned three kinds of dental light irradiators (TP, LM, A95), the cured bodies were measured for their hardness by the method described below. Namely, a mold (the thickness of 1.0 mm) of a polytetrafluoroethylene having a hole measuring 6 mm in diameter x was filled with a paste of a photo-curable composition, and pressed with a polypropylene film. Light was irradiated for a predetermined period of time with the irradiation port of the dental irradiator closely contacted to the polypropylene film thereby to prepare a cured body which was used as a test piece. The length of a diagonal line of a dent was measured, the dent being formed in the test piece by the Vicker's press of a microhardness tester (Model MHT-1 manufactured by Matsusawa Seiki Co.) under a load of 100 gf for a load-holding time of 30 seconds. The time for irradiating the light was 10 seconds when the TP and the LM were used, and was 3 seconds when the A95 was used unless stated otherwise.

(5) Evaluation of preservation stability.
The photo-curable composite resin was preserved in an incubator maintained at 50° C. shutting off the light, and the cured body was measured for its Vicker's hardness after every predetermined interval. The preservation stability was evaluated from a change in the obtained Vicker's hardness with the passage of time.

(6) Environmental light stability testing.

The distance between the source of light and the sample was so set that the light intensity was 10000 luxes on the surface of the composite resin paste sample. A 15-watt fluorescent lamp (Palook, trade name, manufactured by Matsushita Denki Co.) was used as a source of light, and the distance between the sample and the fluorescent lamp was so set that the intensity of illumination measured by using the illuminometer was equal to the above intensity of illumination. The luminous intensity on the irradiated surface was 0.4 mW/cm². 0.03 Grams of the paste of the prepared photo-curable composite resin was weighed, placed on the polypropylene film and was irradiated with the light from the above fluorescent lamp for a predetermined period of time. The sample was, then, depressed to measure the time when the interior of the sample started solidifying. The interval for irradiation was 5 seconds. The longer the time, the more excellent the stability against the environmental light, and a good operation margin time was obtained. The illuminometer was a digital lux meter, FLX-1330 manufactured by Tokyo Garasu Kikaisha Co. The illuminometer possessed a sensitivity over a range of 400 to 700 nm.

(7) Bending strength.

The curable composite resin paste was filled in a stainless steel frame and was irradiated with the light from one surface three times each for 10 seconds in a state of being pressed with the polypropylene with the irradiation port of the light irradiator "TP" being closely contacted to the polypropylene while changing the place, so that the entire composition was irradiated with the light. The irradiation was effected even from the opposite surface three times each for 10 seconds with the irradiation port being closely contacted to the polypropylene thereby to obtain a cured product. The cured body was shaped into a square pole measuring 2×2×25 mm by using a water-resistant polishing paper of #800. The test piece was mounted on a tester (Autograph AG5000D manufactured by Shimazu Mfg. Co.), and a three-point bending rupture strength was measured at a fulcrum distance of 20 mm and a crosshead speed of 1 mm/min.

(8) Change in the color tone.

The paste of the curable composition was filled in a polyacetal mold for producing a disk-like test piece having a diameter of 15 mm and a thickness of 1 mm, pressed with the polypropylene film, and was irradiated with the light at five places each for 10 seconds such that the whole resin is irradiated with the light from the dental light irradiator (TP). One-half of the test piece was covered with an aluminum foil and was directly exposed to the sunlight for a total of 10 hours. The portion covered with the aluminum foil and the portion directly exposed to the sunlight were measured for their color tones by using a spectro photo meter (TC-1800MKII manufactured by Tokyo Denshoku Co.), and the amount of change was expressed as $\Delta E^*$.

$$\Delta E^* = (\Delta L^{*2} + \Delta a^{*2} + \Delta b^{*2})^{1/2}$$

$$\Delta L^* = L_1^* - L_2^*$$

$$\Delta a^* = a_1^* - a_2^*$$

$$\Delta b^* = b_1^* - b_2^*$$

$L_1^*$: brightness index of unexposed portions
$a_1^*$, $b_1^*$: color quality indexes of unexposed portions
$L_2^*$: brightness index of exposed portions
$a_2^*$, $b_2^*$: color quality indexes of exposed portions
$\Delta E^*$: amount of change in the color tone Example 1

As the polymerizable monomers, there were used D-2.6E (70 parts by mass), 3G (25 parts by mass) and UDMA (5 parts by mass), and to which were added the polymerization initiators, i.e., CQ (0.3 parts by mass), DMPT (0.25 parts by mass), DMEM (0.25 parts by mass) and TCT (0.4 parts by mass). The mixtures was dissolved in a dark place to obtain a homogeneous solution thereof. By using three kinds of dental irradiators (LM, A95, TP), the solution was evaluated for its curability and Vicker's hardness. The results were as shown in Table 1.

Comparative Example 1

A solution was prepared in the same manner as in Example 1 but using the DMPT which is an aromatic amine in an amount of 0.5 parts by mass instead of using the DMEM which is the aliphatic amine. The solution was evaluated for its curability and Vicker's hardness. The results were as shown in Table 1.

Comparative Example 2

A solution was prepared in the same manner as in Example 1 but using the DMEM which is an aliphatic amine in an amount of 0.5 parts by mass instead of using the DMPT which is the aromatic amine. The solution was evaluated for its curability and Vicker's hardness. The results were as shown in Table 1.

TABLE 1

| | | | Source of light | | | | | | | |
|---|---|---|---|---|---|---|---|---|---|---|
| | Amine | | LM | | | | A95 | | | TP |
| | Compound | | Curability | | | | Curability | | | Curability |
| | DMPT | DMEM | 3 sec. | 4 sec. | 5 sec. | Hardness | 1 sec. | 2 sec. | 3 sec. | Hardness | 5 sec. | Hardness |
| Ex. 1 | 0.25 | 0.25 | 1.5 | 5.0 | 6.0 | 14 | 3.0 | 5.5 | 6.5 | 16 | ○ | 21 |
| Comp. Ex. 1 | 0.5 | — | X | X | 2.0 | 13 | X | X | 5.0 | 7 | ○ | 16 |
| Comp. Ex. 1 | — | 0.5 | X | 3.5 | 6.0 | 11 | 2.0 | 5.0 | 6.0 | 7 | ○ | 14 |

*: Evaluation X with LM and A95 means that the cured bodies have zero diameter.

As demonstrated in Example 1, the curable composition of the present invention using the aliphatic amine and the aromatic amine in combination undergoes the curing very quickly even with a weak source of light such as a laser diode (LM), and is cured favorably. When either the aliphatic amine only or the aromatic amine only is used as shown in Comparative Examples 1 and 2, on the other hand, the curing requires an extended period of time, and the cured bodies exhibit low hardness.

Examples 2 and 3, Comparative Examples 3 to 6

The solutions were prepared in the same manner as in Example 1 but changing the composition of the polymerization initiator as shown in Table 2, and were evaluated. The curability was evaluated by using a halogen lamp (TP). The results were as shown in Table 2.

cases, the curing required further elongated times than when the triazine compound was not blended. The Vicker's hardness was so low as could not be measured. Comparative Example 6 has used the aryl iodonium salt which is a photo acid generating agent like the triazine compound. In this case, the curability was poorer than that of Comparative Example 1.

Examples 4 to 10, Comparative Examples 7 to 11

To 100 parts by weight of the polymerizable monomers comprising D-2.6E (70 parts by mass), 3G (25 parts by mass) and UDMA (5 parts by mass), there were added E-1

TABLE 2

| | Photopolymerization initiator/parts by mass | | | | | TP curability | | | Hardness | | |
|---|---|---|---|---|---|---|---|---|---|---|---|
| | CQ | DMPT | DMEM | TCT | Ph2IPF6 | 5 sec. | 10 sec. | 15 sec. | LM | A95 | TP |
| Ex. 2 | 0.15 | 0.25 | 0.25 | 0.4 | — | ○ | | | 11 | 12 | 15 |
| Ex. 3 | 0.3 | 0.25 | 0.25 | 0.4 | — | ○ | | | 12 | 11 | 16 |
| Comp. Ex. 3 | 0.3 | 0.25 | 0.25 | — | — | X | Δ | Δ | 4 | 3 | 9 |
| Comp. Ex. 4 | 0.3 | — | — | 0.4 | — | X | X | Δ | could not be measured | could not be measured | could not be measured |
| Comp. Ex. 5 | — | 0.25 | 0.25 | 0.4 | — | X | X | X | could not be measured | could not be measured | could not be measured |
| Comp. Ex. 6 | 0.3 | 0.5 | — | — | 0.4 | Δ | ○ | | 9 | 8 | 13 |

Comparative Example 3 was not blended with the triazine compound which is one of the essential components of the photopolymerization initiator of the present invention. In this case, the curing rate was very slower than that of the Examples that were blended with the triazine compound. Further, the Vicker's hardness was very lower than that of the Examples. Comparative Example 5 was not blended with the α-diketone compound and Comparative Example 4 was not blended with the amine compound at all. In these (140 parts by mass) and E-3 (60 parts by mass) as inorganic fillers and HQME (0.15 parts by mass) as a polymerization inhibitor to prepare paste-like compositions. To the compositions were further added the photopolymerization initiators of the compositions shown in Table 3 to obtain curable composite resin paste. The composite resin paste was measured for their stability against the environmental light, hardness and bending strength. The results were as shown in Table 3.

TABLE 3

| | Photopolymerization initiator/parts by mass | | | | Stability to environmental light sec. | Hardness | | | Bending strength MPa |
|---|---|---|---|---|---|---|---|---|---|
| | α-Diketone | Aliphatic amine | Aromatic amine | Triazine compound | | LM | A95 | TP | |
| Ex. 4 | CQ 0.2 | DMEM 0.1 | DMPT 0.23 | TCT 0.4 | 35 | 25 | 27 | 35 | 138 |
| Ex. 5 | CQ 0.2 | TEOA 0.35 | DMBE 0.35 | TCT 0.4 | 40 | 24 | 30 | 37 | 140 |
| Ex. 6 | CQ 0.2 | MDEOA 0.25 | DMBE 0.25 | TCT 0.3 | 40 | 24 | 25 | 35 | 128 |
| Ex. 7 | CQ 0.2 | TAA 0.25 | DMBE 0.25 | TCT 0.3 | 35 | 23 | 23 | 34 | 130 |
| Ex. 8 | CQ 0.2 | EDEOA 0.25 | DMBE 0.25 | TCT 0.3 | 35 | 24 | 27 | 35 | 130 |
| Ex. 9 | CQ 0.2 | DMEM 0.35 | DMPT 0.35 | PBCT 0.3 | 35 | 20 | 26 | 36 | 140 |
| Ex. 10 | CQ 0.2 | TEOA 0.25 | DMBE 0.25 | MPBCT 0.3 | 35 | 16 | 15 | 29 | 126 |
| Comp. Ex. 7 | CQ 0.3 | DMEM 0.1 | DMPT 0.23 | — | 25 | <5 | <5 | <5 | <50 |
| Comp. Ex. 8 | CQ 0.2 | — | — | TCT 0.4 | >50 | could not be measured | could not be measured | could not be measured | could not be measured |
| Comp. Ex. 9 | — | DMEM 0.1 | DMPT 0.23 | TCT 0.4 | >50 | could not be measured | could not be measured | could not be measured | could not be measured |
| Comp. Ex. 10 | CQ 0.2 | DMEM 0.3 | — | TCT 0.4 | 45 | 13 | 7 | 26 | 120 |
| Comp. Ex. 11 | CQ 0.2 | — | DMPT 0.45 | TCT 0.4 | 25 | 10 | 6 | 32 | 130 |

As will be understood from the results shown in Table 3, the curable compositions using the photopolymerization initiators of the present invention exhibit excellent stability against the environmental light, and the cured bodies thereof exhibit favorable mechanical properties. In any Example, further, the curing was completed in less than 5 seconds when the halogen lamp (TP) was used.

Examples 11 and 12, Comparative Examples 12 to 14

The curable composite resin paste same as those of Example 4 were prepared but using the photopolymerization initiators of the compositions shown in Table 4. The cured composite resins were evaluated for their Vicker's hardness while setting the light irradiation time to be 30 seconds when the TP or the LM was used and setting the light irradiation time to be 10 seconds when the A95 was used. Similarly, the cured bodies were measured for their bending strength by irradiating the light using the TP three times each for 30 seconds. The results were as-shown in Table 4.

properties are obtained even by using the light irradiators (A95, LM) employing the xenon lamp and the laser diode as sources of light.

In Comparative Examples 12 to 14, however, the cured bodies obtained by using the light irradiators (A95, LM) fail to exhibit properties to a sufficient degree.

Examples 13 and 14, Comparative Examples 12 to 14

To 100 parts by weight of the polymerizable monomers comprising Bis-GMA(60 parts by mass) and 3G (40 parts by mass), there were added E-2 (160 parts by mass) and E-4 (240 parts by mass) as inorganic fillers and HQME (0.15 parts by mass) as a polymerization inhibitor to prepare paste-like compositions. To the compositions were further added the photopolymerization initiators of the compositions shown in Table 5 to obtain photo-curable composite

TABLE 4

| | Photopolymerization initiator/parts by mass | | | | Hardness after irradiated for extended periods of time | | | Bending strength after irradiated for extended priods |
|---|---|---|---|---|---|---|---|---|
| | α-Diketone | Aliphatic amine | Aromatic amine | Triazine compound | LM | A95 | TP | of time/MPa |
| Ex. 11 | CQ 0.2 | DMEM 0.1 | DMPT 0.23 | TCT 0.4 | 34 | 40 | 49 | 148 |
| Ex. 12 | CQ 0.2 | TEOA 0.25 | DMBE 0.25 | TCT 0.4 | 38 | 44 | 48 | 156 |
| Comp. Ex. 12 | CQ 0.2 | DMEM 0.3 | — | TCT 0.4 | 25 | 20 | 47 | 126 |
| Comp. Ex. 13 | CQ 0.3 | DMEM 0.1 | DMPT 0.23 | — | 3 | could no be measured | 18 | 88 |
| Comp. Ex. 14 | CQ 0.3 | — | DMPT 0.63 | — | 13 | 14 | 21 | 105 |

As illustrated in Examples and in Comparative Examples above, the mechanical properties of the obtained cured bodies are improved as the time for irradiation with light is lengthened. In Examples 11 and 12 blended with the light polymerization initiators of the present invention, good paste. The curable composite paste was all cured in less than 5 seconds when the halogen lamp was used. The curable composite resin paste was measured for the stability against the environmental light, hardness and bending strength. The results were as shown in Table 5.

TABLE 5

| | Photopolymerization initiator/parts by mass | | | | Stability to environmental light sec. | Vicker's hardness | | | Bending strength MPa |
|---|---|---|---|---|---|---|---|---|---|
| | α-Diketone | Aliphatic amine | Aromatic amine | Triazine compound | | LM | A95 | TP | |
| Ex. 13 | CQ 0.2 | DMEM 0.05 | DMPT 0.15 | TCT 0.4 | 35 | 21 | 36 | 37 | 155 |
| Ex. 14 | CQ 0.2 | TEOA 0.25 | DMBE 0.25 | TCT 0.4 | 35 | 25 | 36 | 39 | 150 |
| Comp. Ex. 15 | CQ 0.2 | DMEM 0.5 | — | TCT 0.4 | 35 | 14 | 22 | 30 | 118 |
| Comp. Ex. 16 | CQ 0.2 | — | DMPT 0.35 | TCT 0.4 | 25 | 16 | 20 | 36 | 148 |

Example 15

To 100 parts by weight of the polymerizable monomers comprising Bis-GMA(60 parts by mass) and 3G (40 parts by mass), there were added E-1 (105 parts by mass) and E-3 (45 parts by mass) as inorganic fillers, HQME (0.15 parts by mass) as a polymerization inhibitor, and CQ (0.2 parts by mass), TEOA (0.25 parts by mass), DMBE (0.25 parts by mass) and TCT (0.2 parts by mass) as photopolymerization initiators to prepare a resin composite paste.

By using the light irradiator LM, the curable composite resin paste was evaluated for its preservation stability. The results were as shown in Table 6.

Examples 16 to 21, Comparative Examples 15 and 16

A photo-curable composite resin paste was prepared in the same manner as in Example 15 but using the photopolymerization initiators of the compositions shown in Table 6, and were evaluated for their preservation stabilities. The results were as shown in Table 6.

Example 22

A photo-curable composite resin paste was obtained in the same manner as in Example 15 but using the photopolymerization initiator having a composition shown in Table 7. By using the light irradiator LM or TP, the curable composite paste was evaluated for its preservation stability. The results were as shown in Table 7.

Examples 23 to 27, Comparative Examples 17 to 20

A photo-curable composite resin paste was prepared in the same manner as in Example 22 but using the photopolymerization initiators of the compositions shown in Table 7 and was evaluated for the preservation stability. The results were as shown in Table 7.

TABLE 6

| | Photopolymerization initiator/parts by mass | | | | LM Vicker's hardness | | |
| --- | --- | --- | --- | --- | --- | --- | --- |
| | α-Diketone | Aliphatic amine | Aromatic amine | Triazine compound | Preservation period | | |
| | | | | | 0 day | 7 days | 14 days |
| Ex. 15 | CQ 0.2 | TEOA 0.25 | DMBE 0.25 | TCT 0.2 | 31 | 29 | 26 |
| Ex. 16 | CQ 0.2 | TEOA 0.35 | PEAT 0.35 | TCT 0.3 | 25 | 20 | 18 |
| Ex. 17 | CQ 0.2 | EDEOA 0.25 | DMBE 0.25 | TCT 0.2 | 31 | 30 | 20 |
| Ex. 18 | CQ 0.2 | MDEOA 0.25 | DMBE 0.25 | TCT 0.2 | 30 | 28 | 19 |
| Ex. 19 | CQ 0.2 | TAA 0.25 | DMBE 0.25 | TCT 0.2 | 29 | 27 | 19 |
| Ex. 20 | CQ 0.2 | DMEM 0.1 | DMPT 0.23 | TCT 0.4 | 28 | 14 | 12 |
| Ex. 21 | CQ 0.2 | DMEM 0.25 | DMBE 0.25 | TCT 0.2 | 27 | 10 | 8 |
| Comp. Ex. 17 | CQ 0.2 | MDEOA 0.50 | — | TCT 0.2 | 18 | 3 | 3 |
| Comp. Ex. 18 | CQ 0.2 | — | DMBE 0.50 | TCT 0.2 | 10 | 3 | 3 |
| Comp. Ex. 19 | CQ 0.2 | TEOA 0.25 | DMBE 0.25 | — | 6 | 6 | 5 |
| Comp. Ex. 20 | CQ 0.3 | TEOA 0.25 | DMBE 0.25 | — | 7 | 6 | 6 |

TABLE 7

| | Photopolymerization initiator/parts by mass | | | | Vicker's hardness | | | | | |
| --- | --- | --- | --- | --- | --- | --- | --- | --- | --- | --- |
| | | | | | LM | | | TP | | |
| | α-Diketone | Aliphatic amine | Aromatic amine | Triazine compound | Preservation period | | | Preservation period | | |
| | | | | | 0 day | 7 days | 14 days | 0 day | 7 days | 14 days |
| Ex. 22 | CQ 0.2 | DMEM 0.25 | DMPT 0.25 | PBCT 0.40 | 21 | 21 | 21 | 38 | 36 | 36 |
| Ex. 23 | CQ 0.2 | DMEM 0.25 | DMBE 0.25 | PBCT 0.40 | 19 | 20 | 20 | 37 | 37 | 36 |
| Ex. 24 | CQ 0.2 | DEEOA 0.25 | DMPT 0.25 | PBCT 0.40 | 19 | 18 | 18 | 32 | 30 | 30 |
| Ex. 25 | CQ 0.2 | TEA 0.25 | DMPT 0.25 | CBCT 0.40 | 22 | 19 | 17 | 34 | 32 | 29 |
| Ex. 26 | CQ 0.2 | DMEM 0.1 | DMPT 0.23 | TCT 0.4 | 28 | 14 | 12 | 37 | 36 | 36 |
| Ex. 27 | CQ 0.2 | DMEM 0.25 | DMBE 0.25 | TCT 0.20 | 27 | 10 | 8 | 36 | 15 | 14 |
| Comp. Ex. 21 | CQ 0.2 | DMEM 0.50 | — | TCT 0.40 | 10 | 3 | 3 | 25 | 12 | 10 |
| Comp. Ex. 22 | CQ 0.2 | — | DMPT 0.50 | MBCT 0.40 | 17 | 9 | 3 | 31 | 21 | 17 |

TABLE 7-continued

| | Photopolymerization initiator/parts by mass | | | | Vicker's hardness | | | | | |
|---|---|---|---|---|---|---|---|---|---|---|
| | | | | | LM | | | TP | | |
| | α- | Aliphatic | Aromatic | Triazine | Preservation period | | | Preservation period | | |
| | Diketone | amine | amine | compound | 0 day | 7 days | 14 days | 0 day | 7 days | 14 days |
| Comp. Ex. 23 | CQ 0.2 | DMEM 0.50 | — | PBCT 0.40 | 14 | 11 | 8 | 23 | 21 | 21 |
| Comp. Ex. 24 | CQ 0.2 | — | DMBE 0.50 | PBCT 0.40 | 10 | 5 | 3 | 18 | 13 | 10 |

As shown in FIGS. 6 and 7, the curable compositions using the photopolymerization initiators of the present invention provides cured bodies having a high Vicker's hardness even after preserved at a temperature as high as 50° C. for 14 days.

As will be understood from the comparison of Examples 15 to 19 with Examples 20 and 21, further, when there is used a triazine compound (TCT) without organic group bonded through an unsaturated bond that is capable of conjugating with a triazine ring, the curable composition exhibits further excellent preservation stability if the aliphatic amine compound that is used has two or three saturated aliphatic groups substituted with electron attractive groups.

On the other hand, as will be understood from the comparison of Examples 22 to 25 with Examples 26 and 27, when there is used an aliphatic amine compound having only one saturated aliphatic group substituted with the electron attractive group, the curable composition exhibits further excellent preservation stability if the triazine compound that is used has an organic group bonded through an unsaturated bond capable of conjugating with a triazine ring.

Examples 28 to 31, Comparative Examples 21 to 24

A photo-curable composite resin paste was obtained in the same manner as in Example 15 but using the photopolymerization initiators of the compositions shown in Table 8. The curable composite resin paste was all cured in less than 5 seconds when the halogen lamp was used. The curable composite resin paste was measured for the stability against the environmental light, hardness and bending strength. The results were as shown in Table 8.

Table 8 illustrates a case where the blending amount of the α-diketone is varied. As shown in this Table 8, the stability against the environmental light is improved as the blending amount of the α-diketone is decreased. The curable composition blended with the photopolymerization initiator of the present invention exhibits favorable curability even when its stability against the environmental light remains as long as 70 seconds.

Examples 32

To 100 parts by weight of the polymerizable monomers comprising Bis-GMA(60 parts by mass) and 3G (40 parts by mass), there were added E-1 (140 parts by mass) and E-3 (60 parts by mass) as inorganic fillers, HQME (0.15 parts by mass) and BHT (0.02 parts by mass) as a polymerization inhibitor, CQ (0.2 parts by mass), MDEOA (0.3 parts by mass), PMAN (0.2 parts by mass) and TCT (0.3 parts by mass) as photopolymerization initiators, and titanium dioxide in an amount of 160 ppm, pigment yellow 95 in an amount of 5 ppm, pigment red 166 in an amount of 1.2 ppm and pigment blue 60 in an amount of 0.8 ppm as pigments to prepare a photo-curable composite resin paste.

A change in the color tone was evaluated to be as shown in Table 9.

Example 33

A photo-curable composite resin paste was obtained in the same manner as in Example 32 but using DMBE (0.2 parts by mass) as the aromatic amine. A change in the color tone was evaluated to be as shown in Table 9.

TABLE 8

| | Photopolymerization initiator/parts by mass | | | | Stability to environmental light sec. | Hardness | | | Bending strength |
|---|---|---|---|---|---|---|---|---|---|
| | α-Diketone | Aliphatic amine | Aromatic amine | Triazine compound | | TP | LM | A95 | MPa |
| Ex. 28 | CQ 0.10 | TEOA 0.25 | DMBE 0.25 | TCT 0.30 | 70 | 38 | 20 | 30 | 142 |
| Ex. 29 | CQ 0.20 | TEOA 0.25 | DMBE 0.25 | TCT 0.30 | 40 | 40 | 26 | 31 | 146 |
| Ex. 30 | CQ 0.30 | TEOA 0.25 | DMBE 0.25 | TCT 0.30 | 30 | 39 | 28 | 30 | 147 |
| Ex. 31 | CQ 0.40 | TEOA 0.25 | DMBE 0.25 | TCT 0.30 | 20 | 40 | 32 | 31 | 146 |

TABLE 9

|  | Photopolymerization initiator/parts by mass | | | | Change in color tone | Hardness | | |
| --- | --- | --- | --- | --- | --- | --- | --- | --- |
|  | α-Diketone | Aliphatic amine | Aromatic amine | Triazine compound | $\Delta E^*$ | LM | A95 | TP |
| Ex. 32 | CQ 0.2 | MDEOA 0.3 | PMAN 0.2 | TCT 0.3 | 2.90 | 22 | 28 | 34 |
| Ex. 33 | CQ 0.2 | MDEOA 0.3 | PMAN 0.2 | TCT 0.3 | 4.52 | 24 | 36 | 36 |

The invention claimed is:

1. A one-paste photopolymerizable composition comprising a photopolymerization initiator and an ethylenically unsaturated monomer, wherein said photopolymerization initiator comprises
   0.01 to 10 parts by mass of an α-diketone compound (A) per 100 parts by mass of said ethylenically unsaturated monomer,
   10 to 1000 parts by mass of an amine compound (B) per 100 parts by mass of said α-diketone compound (A) and
   5 to 1000 parts by mass of an s-triazine compound (C) having a trihalomethyl group as a substituent per 100 parts by mass of said α-diketone compound (A),
   the amine compound (B) containing an aliphatic amine compound (B1) and an aromatic amine compound (B2) at a mass ratio of B1:B2=3:97 to 97:3.

2. A one-paste photopolymerizable composition according to claim 1, wherein the aliphatic amine compound (B1) has a tertiary amino group in which three saturated aliphatic groups are bonded to a nitrogen atom, and at least two of said saturated aliphatic groups have electron attractive groups as substituents.

3. A one-paste photopolymerizable composition according to claim 1, wherein the aromatic amine compound (B2) is represented by the following general formula,

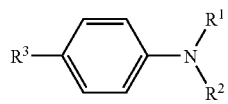

wherein $R^1$ and $R^2$ are, independently from each other, alkyl groups, and $R^3$ is an alkyloxycarbonyl group.

4. A one-paste photopolymerizable composition according to claim 1, wherein the s-triazine compound (C) has, as a substituent, an organic group that has an unsaturated bond capable of conjugating with the triazine ring.

5. A method of using a one-paste photopolymerizable composition as a dental material comprising the steps of applying and photopolymerizing the one-paste photopolymerizable composition according to claim 1.

6. A one-paste photopolymerizable dental composite resin comprising a photopolymerization initiator, an ethylenically unsaturated monomer without acid group (D) and an inorganic filler (E),
   wherein said photopolymerization initiator comprises 0.01 to 10 parts by mass of an α-diketone compound (A) per 100 parts by mass of said ethylenically unsaturated monomer,
   10 to 1000 parts by mass of an amine component (B) per 100 parts by mass of said α-diketone compound (A) and 5 to 1000 parts by mass of an s-triazine compound (C) having a trihalomethyl group as a substituent per 100 parts by mass of said α-diketone compound (A),
   the amine component (B) containing an aliphatic amine compound (B1) and an aromatic amine compound (B2) at a mass ratio of B1:B2=3:97 to 97:3.

* * * * *